United States Patent
Frey et al.

(10) Patent No.: US 6,268,510 B1
(45) Date of Patent: Jul. 31, 2001

(54) REARRANGEMENT PROCESS AND TRICYCLIC AND TETRACYCLIC COMPOUNDS

(75) Inventors: Lisa F. Frey, Somerset; Edward J. J. Grabowski, Westfield, both of NJ (US); Stephane G. Ouellet, Toronto (CA); Robert A. Reamer, Bloomfield; Richard D. Tillyer, Cranford, both of NJ (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/610,780

(22) Filed: Jul. 6, 2000

Related U.S. Application Data

(60) Provisional application No. 60/143,108, filed on Jul. 9, 1999.

(51) Int. Cl.[7] ................................................. C07D 487/12
(52) U.S. Cl. ............................................................ 548/428
(58) Field of Search ............................................... 548/428

(56) References Cited

PUBLICATIONS

Vice, Susan F., et al., Tetrahedron Lett., vol. 26(2), pp. 165–168, 1985.*
Dobbs, Adrian P., et al. Tetrahedron, vol. 54, pp. 2149–2160, 1998.*
Eisch, J.J., et al., J. Org. Chem., vol. 36(22), pp. 3376–3381, 1971.
Rathjen, H–J, et al., J. Am. Chem. Soc., vol. 113, pp. 3904–3909, 1991.
von E. Doering, W., et al., J. Am. Chem. Soc., vol. 72, pp. 2305–2306, 1950.
Taber, D.F., et al., J. Am. Chem. Soc., vol. 108, pp. 7686–7693, 1986.
Russell, G.A., et al., J. Org. Chem., vol. 28, pp. 1933–1934, 1963.
Johnson, R.P., Chem. Rev., vol. 89, pp. 1111–1124, 1989.
Burrell, R.C., et al., J. Am. Chem. Soc., vol. 118, pp. 4218–4219, 1996.
Hopf, H, et al., Angew. Chem. Int. Ed. Engl., vol. 36(11), pp. 1187–1190, 1997.
Wiebe, J.M., et al., Tetrahedron, vol. 52(36), pp. 11705–11724, 1996.
Gupta, Y.N., et al., J. Am. Chem. Soc., vol. 104, pp. 7336–7338, 1982.
Verboom, W, et al., Tet. Lett., vol. 24(36), pp. 3923–3926, 1983.
Vanderzande, D.J., et al., J. Org. Chem., vol. 48, pp. 2188–2193, 1983.
Khasanova, T., et al., J. Am. Chem. Soc., vol. 122, pp. 8585–8586, 2000.

* cited by examiner

*Primary Examiner*—Deborah C. Lambkin
*Assistant Examiner*—Andrea M. D'Souza
(74) *Attorney, Agent, or Firm*—Valerie J. Camara; Mark R. Daniel

(57) ABSTRACT

A rearrangement process for the preparation of a 6,5,5-tricyclic, a 6,6,5-tricyclic and 6,5,5,7-tetracyclic ring system is disclosed.

2 Claims, 1 Drawing Sheet

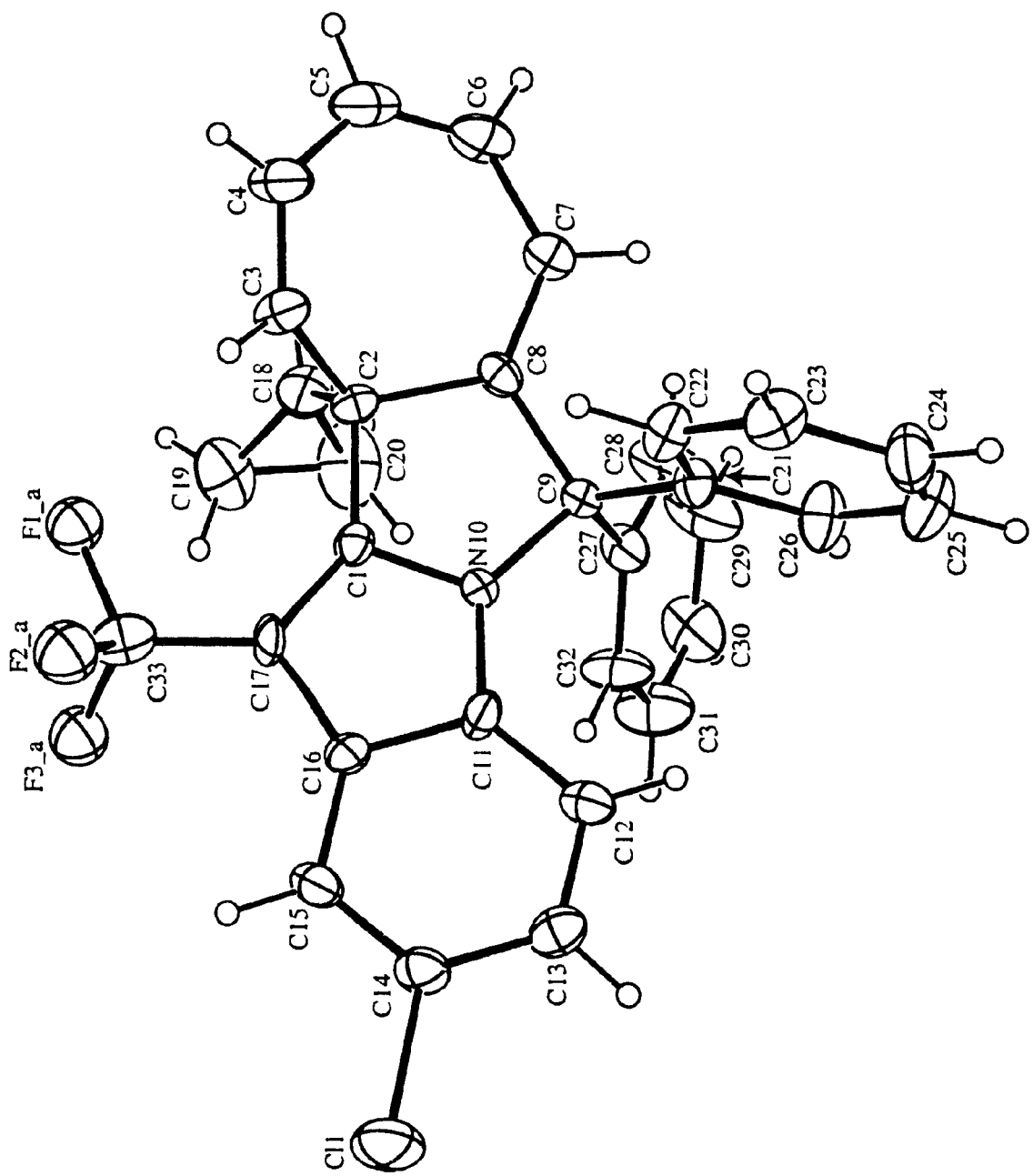

REARRANGEMENT PROCESS AND TRICYCLIC AND TETRACYCLIC COMPOUNDS

This application claims the benefit under 35 U.S.C. 119(e) of Provisional Application Ser. No. 60/143,108 filed on Jul. 9, 1999.

BACKGROUND OF THE INVENTION

This invention was discovered during the process development work on efavirenz (1), a non-nucleoside reverse transcriptase inhibitor currently being sold under the trademarks Stocrin ™ (registered trademark of Merck & Co., Inc.) and Sustiva™ (registered trademark of DuPont Pharmaceuticals Company). A practical synthesis of efavirenz has been developed, based upon asymmetric alkynylation chemistry, which has been implemented for large scale manufacture [a] M. E. Pierce, R. L. Parsons, Jr., L. A. Radesca. Y. S. Lo, S. Silverman, J. R. Moore, Q. Islam, A. Choudhury, J. M. D. Fortunak, D. Nguyen, C. Luo, S. J. Morgan, W. P. Davis, P. N. Confalone, C. Chen, R. D. Tillyer, L. Frey, L. Tan, F. Xu, D. Zhao, A. S. Thompson, E. G. Corley, E. J. J. Grabowski, R. Reamer, P. J. Reider, *J. Org. Chem.,* 1998, 63, 8536–8543. b) Recently, an efficient, protection free process was reported: L. Tan, C. Chen, R. D. Tillyer, E. J. J. Grabowski, P. J. Reider, *Angew. Chem. Int. Ed.,* 1999, 38, 711–713.].

In defining the synthesis of 1, two options were evaluated for conversion of protected propargyl alcohols 2a/2b into the final 1,4-dihydro-2H-3,1-benzoxazin-2-one product. The first involved deprotection of the amino alcohols 2a/2b to give 3, which was reacted with phosgene or with p-nitrophenylchloroformate to give 1. The alternative approach involved ring closure to give the N-protected carbamates 4a or 4b, followed by deprotection. While one of the first routes (p-methoxybenzyl [PMB] protection) was developed into the manufacturing process, investigation of the ring closure reaction of trityl protected propargyl alcohol 2a [M. E. Pierce, et al., *J. Org. Chem.,* 1998, 63, 8536–8543.]uncovered this novel rearrangement chemistry and ring systems.

SUMMARY OF THE INVENTION

The present invention provides for the preparation of a compound of Formula I:

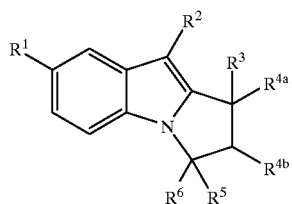

which comprises the steps of:

a) reacting a compound of Formula II

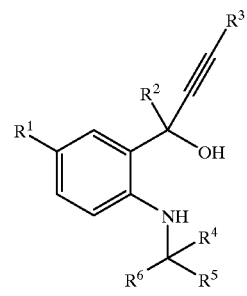

with carbonyl diimidazole in an aprotic solvent, or alternatively with acetic anhydride in a solvent to produce a protected alcohol of Formula III:

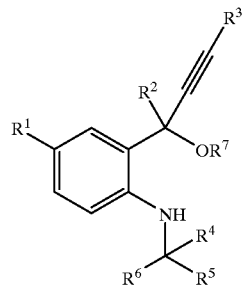

b) heating the protected alcohol of Formula III in a solvent at a temperature of about 50° C. to about 80° C. to produce the compound of Formula I.

Also within the scope of the invention is the process as recited above wherein step (a) is omitted. Additionally, the scope of the invention includes the compounds of Formula I and IV, which is shown below:

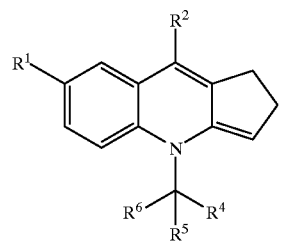

BRIEF DESCRIPTION OF THE DRAWING

FIGURE X-ray diffraction analysis of Compound 5a, substituted dihydrocyclohepta[3,4]pyrrolo [1,2-a]indole.

DETAILED DESCRIPTION OF THE INVENTION

The present invention provides for the preparation of compound of Formula I:

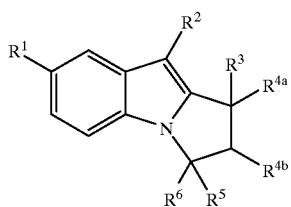

I wherein:

R¹ is: H, or halo;

R² is: C₁–C₆ alkyl, C₁–C₆ perfluoroalkyl, or phenyl;

R³ is: H, C₁–C₆ alkyl, C₃–C₆ cycloalkyl, CO₂Et, phenyl, unsubstituted or substituted with one, two, or three substituents selected from C₁–C₆ alkyl, C₁–C₆ alkoxyl, and nitro;

R⁴, R⁵ and R⁶ are H, C₁–C₆ alkyl, or phenyl, unsubstituted or substituted with one, two, or three Ra substituents selected from: C₁–C₆ alkyl, C₁–C₆ alkoxyl, SO₂CH₃;

R⁴ᵃ is: H and R⁴ᵇ is C₁–C₅ alkyl, when R⁴ is C₁–C₆ alkyl, or

R⁴ᵃ and R⁴ᵇ substitutents together represent a ring of seven carbons with alternating double bonds, that is unsubstituted or substituted with one, two, or three Rᵃ substituents selected from: C₁–C₆ alkyl, C₁–C₆ alkoxyl, SO₂CH₃, when R⁴ represents a phenyl, as defined above in R⁴; and R⁷ is: —CO(CH₃) or —CO(imidazolyl);

which comprises the steps of:

a) reacting a compound of Formula II

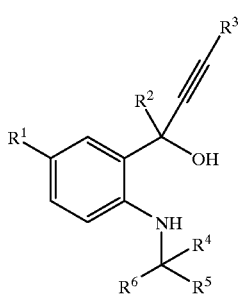

II with carbonyl diimidazole in an aprotic solvent, or alternatively with acetic anhydride in a solvent to produce a protected alcohol of Formula III:

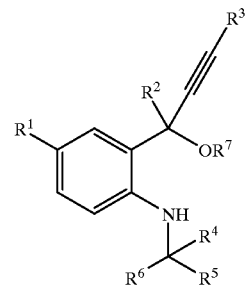

III b) heating the protected alcohol of Formula III in a solvent or neat at a temperature of about 0° C. to about 100° C. to produce the compound of Formula I, with the proviso that when R³ is cyclopropyl, R⁴ and R⁵ are H, and R⁶ is phenyl, unsubstituted or substituted with one, two, or three Rᵃ substituents selected from: C₁–C₆ alkyl, C₁–C₆ alkoxyl, SO₂CH₃, the compound of Formula IV:

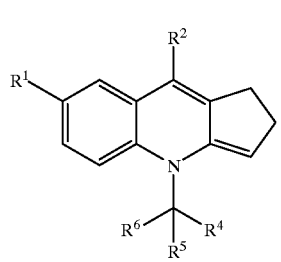

IV is produced.

The present invention also provides for the preparation of a a compound of Formula I

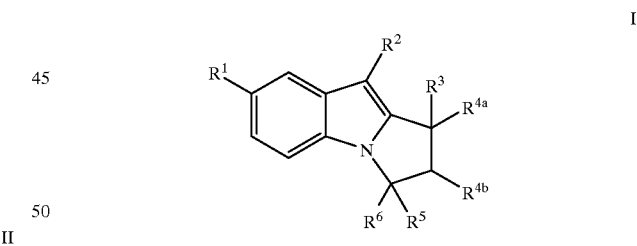

I wherein:

R¹ is: H, or halo;

R² is: C₁–C₆ alky, C₁–C₆ perfluoroalkyl, or phenyl;

R³ is: H, C₁–C₆ alky, C₃–C₆ cycloalkyl, CO₂Et, phenyl, unsubstituted or substituted with one, two, or three substituents selected from C₁–C₆ alkyl, C₁–C₆ alkoxyl, and nitro;

R⁴, R⁵ and R⁶ are C₁–C₆ alkyl, or phenyl unsubstituted or substituted with one, two, or three Rᵃ substituents selected from C₁–C₆ alkyl, C₁–C₆ alkoxyl, SO₂CH₃;

R⁴ᵃ is: H and R⁴ᵇ is C₁–C₅ alkyl, when R⁴ is C₁–C₆ alkyl, or

R⁴ᵃ and R⁴ᵇ substitutents together represent a ring of seven carbons with alternating double bonds, that is unsubstituted or substituted with one, two, or three $R^a$ substituents selected from: $C_1-C_6$ alkyl, $C_1-C_6$ alkoxyl, $SO_2CH_3$, when $R^4$ represents a phenyl, as defined above in $R^4$; and $R^7$ is: —$CO(CH_3)$ or —$CO(imidazolyl)$;

which comprises reacting a compound of Formula III:

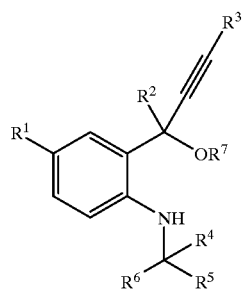

III in a solvent or neat at a temperature of about 0° C. to about 100° C. to produce the compound of Formula I.

A preferred embodiment of the present invention is the process for preparing a compound of Formula Ia:

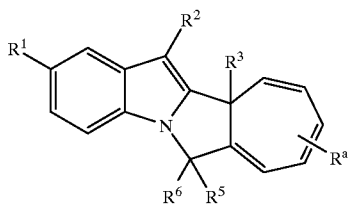

Ia wherein:

$R^1$ is: H, or halo;

$R^2$ is: $C_1-C_6$ perfluoroalkyl, or phenyl;

$R^3$ is: H, $C_1-C_6$ alkyl, $C_1-C_6$ cycloalkyl, $CO_2Et$, phenyl, unsubstituted or substituted with one, two, or three substituents selected from $C_1-C_6$ alkyl, $C_1-C_6$ alkoxyl, and nitro;

$R^4$, $R^5$ and $R^6$ are phenyl unsubstituted or substituted with an $R^a$ substituent selected from $C_1-C_6$ alkyl, $C_1-C_6$ alkoxyl, $SO_2CH_3$, comprises reacting a compound of Formula III:

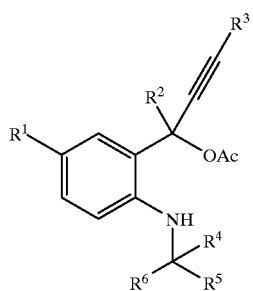

III in acetonitrile or neat at a temperature of about 25° C. to about 80° C.

A compound of Formula I:

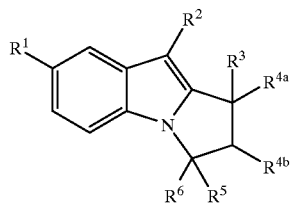

I wherein:

$R^1$ is: H, or halo;

$R^2$ is: $C_1-C_6$ alkyl, $C_1-C_6$ perfluoroalkyl, or phenyl;

$R^3$ is: H, $C_1-C_6$ alkyl, $C_3-C_6$ cycloalkyl, $CO_2Et$, phenyl, unsubstituted or substituted with one, two, or three substituents selected from $C_1-C_6$ alkyl, $C_1-C_6$ alkoxyl, and nitro;

$R^4$, $R^5$ and $R^6$ are H, $C_1-C_6$ alkyl, or phenyl, unsubstituted or substituted with one, two, or three $R^a$ substituents selected from: $C_1-C_6$ alkyl, $C_1-C_6$ alkoxyl, $SO_2CH_3$;

$R^{4a}$ is: H and $R^{4b}$ is $C_1-C_5$ alkyl, when $R^4$ is $C_1-C_6$ alkyl, or $R^{4a}$ and $R^{4b}$ substitutents together represent a ring of seven carbons with alternating double bonds, that is unsubstituted or substituted with one, two, or three $R^a$ substituents selected from: $C_1-C_6$ alkyl, $C_1-C_6$ alkoxyl, $SO_2CH_3$, when $R^4$ represents a phenyl, as defined above in $R^4$.

A preferred embodiment of the invention is a compound of Formula Ia:

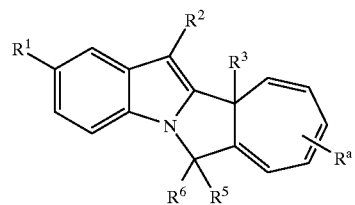

Ia wherein:

$R^1$ is: H, or halo;

$R^2$ is: $C_1-C_6$ perfluoroalkyl, or phenyl;

$R^3$ is: H, $C_1-C_6$ alkyl, $C_1-C_6$ cycloalkyl, $CO_2Et$, phenyl, unsubstituted or substituted with one, two, or three substituents selected from $C_1-C_6$ alkyl, $C_1-C_6$ alkoxyl, and nitro; and $R^4$, $R^5$ and $R^6$ are phenyl unsubstituted or substituted with an $R^a$ substituent selected from $C_1-C_6$ alkyl, $C_1-C_6$ alkoxyl, $SO_2CH_3$.

A compound of Formula IV:

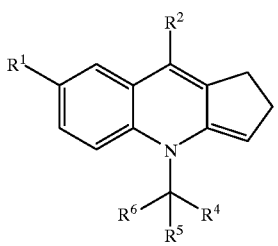

wherein
- $R^1$ is: H, or halo;
- $R^2$ is $C_1$–$C_6$ alkyl, $C_1$–$C_6$ perfluoroalkyl, or phenyl;
- $R^4$ and $R^5$ are H; and
- $R^6$ is phenyl, unsubstituted or substituted with one, two, or three $R^a$ substituents selected from: $C_1$–$C_6$ alkyl, $C_1$–$C_6$ alkoxyl, $SO_2CH_3$.

The aprotic solvents utilized in the formation of the carbonyl imidazole can be non-polar or polar solvents, excluding water and alcohols.

The solvents utilized in the formation of the acetate and rearrangement step are solvents, including but not limited to acetonitrile, tetrahydrofuran, toluene, dimethylacetamide, N-methylpyrrolidinone, dimethylformamide, ethyl acetate, isopropyl acetate, methyl t-butyl ether, hexane, cyclohexane, and butyl acetate. The acetate formation step can be carried out in excess acetic anhydride. Additionally, the rearrangement of the acetate can be carried out in the absence of a solvent (neat).

The temperature range for the preparation of the acetate and carbonylimidazole is about 15° C. to about 80° C., and preferably about 15° C. to about 35° C. The temperature range for rearrangement step is about 0° C. to about 100° C., preferably about 15° C. to about 80° C., and more preferably about 70° C. to about 80° C.

The reaction time for the rearrangement step is about 5 minutes to about 6 weeks, and preferably about 5 hours to about 8 hours.

SCHEME 1

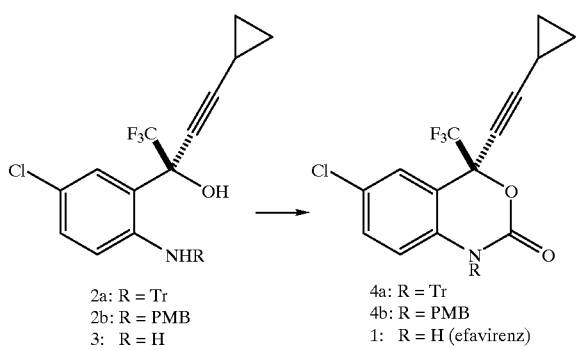

2a: R = Tr
2b: R = PMB
3:   R = H

4a: R = Tr
4b: R = PMB
1:   R = H (efavirenz)

Attempted conversion of the optically active amino alcohol 2a into the cyclic carbamate 4a, using carbonyl diimidazole (CDI, 25° C.) in several solvents did not provide 4a, as expected, but instead resulted in a clean and rapid conversion to the racemic dihydrocyclohepta-[3,4]pyrrolo [1,2-a]indole 5a (Scheme 2). This heterocyclic structure is unprecedented in the literature, and was fully characterized by NMR spectroscopy and by X-ray diffraction analysis (FIG. 1). Formation of 5a apparently proceeds via O-activation with CDI followed by a facile rearrangement featuring ring expansion of one of the phenyl rings of the trityl group.

The discovery of this unexpected and useful rearrangement-ring expansion process prompted further studies to define the structural features in propargyl alcohols 2 which lead to efficient rearrangement, upon O-activation, to give tetracyclic compounds 5 (Scheme 2). In particular, we examined the effect of terminal acetylenic substituents ($R^3$), propargylic substituents ($R^2$) and the N-protecting group ($R^4$, $R^5$, $R^6$) on the outcome (or rate) of the rearrangement process, in order to gain some understanding of the reaction mechanism.

SCHEME 2

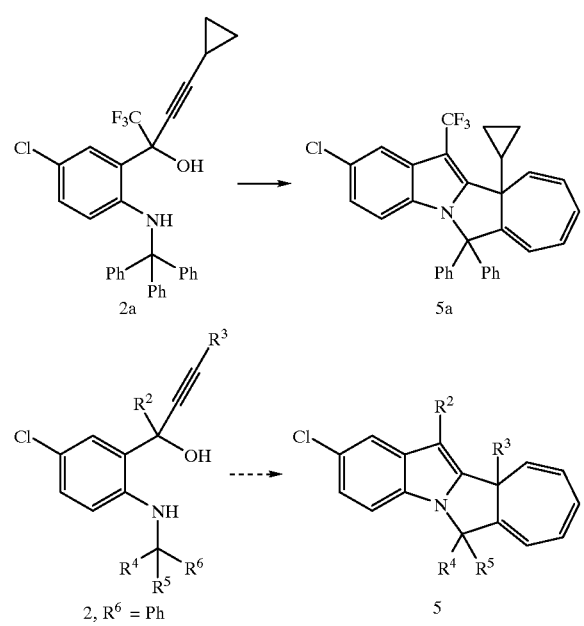

First, a protocol was required for the activation of alcohols 2 which would allow for convenient collection of rate data for the rearrangement. Activation via the acetate was selected for all studies since rearrangements were much slower than those initiated by CDI, and allowed for separation of the activation and rearrangement steps. Thus 2a was converted cleanly into the corresponding O-acetate ($Ac_2O$, DIEA, ACN, 25° C.), which was readily isolated, and then rearranged to 5a simply by heating in solvent. No difference in reaction rate is observed for reactions using the acetate prepared in situ. It was found that the rate of this transformation is similar in a range of organic solvents (first order kinetics, $t_{1/2}$=99 min in ACN). For comparison, in DMAC, $t_{1/2}$=172 min, in EtOAc, $t_{1/2}$=209 min and in toluene, $t_{1/2}$=267 min. It was also shown that the rearrangement of 2a to 5a via the acetate proceeds with racemization (as for CDI activation) and that racemic product arises as a consequence of the rearrangement reaction and not from racemization of the O-acetate of 2a.

Rearrangements of several N-trityl-protected amino alcohols 2 (via the corresponding acetates) with different terminal acetylene substituents (in acetonitrile at about 75° C.) were studied (Table 1). The rearrangement proceeded cleanly in most cases, to give high yields of the tetracyclic product (5). There is a significant terminal acetylene substituent effect on the rate of this rearrangement reaction. In general, rapid and efficient rearrangement was observed for substrates with terminal substituents capable of conjugation with the triple bond (cyclopropyl-entry 1, carboethoxy-entry 2, phenyl-entries 6–9). Slow rearrangements were observed for substrates with terminal substituents incapable of conjugation to the triple bond (H-entry 3, hexyl-entry 4, cyclohexyl-entry 5), with larger substituents providing slowest reaction. For phenyl substitution, no significant effects on the rate of rearrangement were observed with electron donating or withdrawing groups in the para position (entries 6–8). Finally, there is a significant propargyl substituent effect. Replacement of trifluoromethyl in 2g by phenyl (compare entries 6 and 9) provided an approximate 9 fold reduction in half life.

influence the outcome of the reaction. However, no such electronic effect was observed. Rearrangement of 2k [(4-methoxyphenyl)diphenylmethyl] and 2l [(4-sulfonylphenyl)diphenyl-methyl] (Scheme 3) provided essentially equal amounts of three rearrangement products, resulting from ring expansion of the substituted phenyls (5k-c and 5l-c) and the unsubstituted phenyls (diastereomers 5k-a/5k-b and diastereomers 5l-a/5l-b) respectively.

SCHEME 3

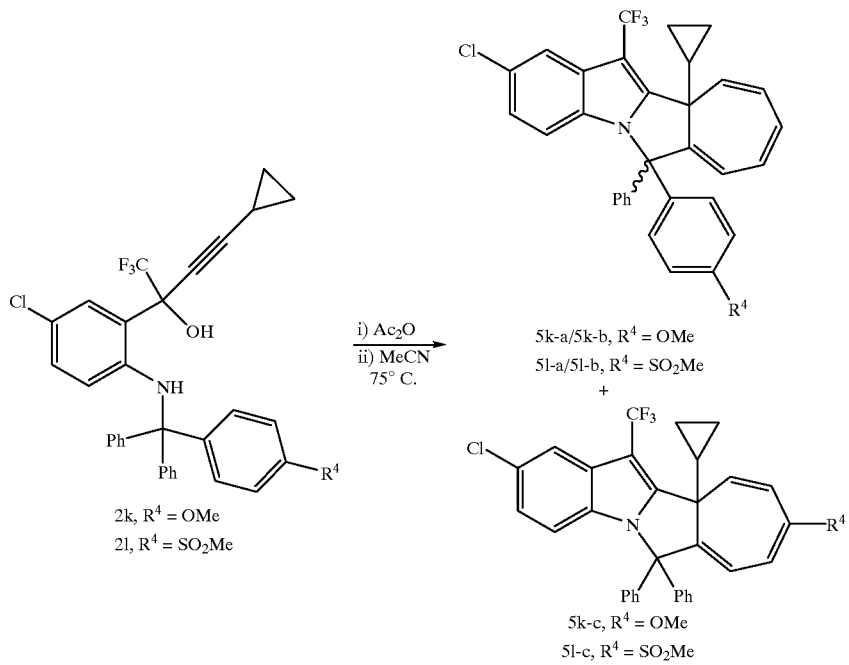

TABLE 1

Rearrangement of amino alcohols 2 ($R^6 = R^5 = R^4 = Ph$).

| Entry | substrate | $R^3$ | $R^2$ | product | $t_{1/2}$[a] | yield %[b] |
|---|---|---|---|---|---|---|
| 1 | 2a | cyclopropyl | $CF_3$ | 5a | 99 min | 84 |
| 2 | 2c | $CO_2Et$ | $CF_3$ | 5c | 131 min | 80 |
| 3 | 2d | H | $CF_3$ | 5d | 9 h | 82 |
| 4 | 2e | n-Bu | $CF_3$ | 5e | 115 h | 96 |
| 5 | 2f | CyHex | $CF_3$ | 5f | 165 h | 40[c] |
| 6 | 2g | Ph | $CF_3$ | 5g | 101 min | 92 |
| 7 | 2h | 4-$NO_2$Ph | $CF_3$ | 5h | 87 min | 97 |
| 8 | 2i | 4-MeOPh | $CF_3$ | 5i | 67 min | 99 |
| 9 | 2j | Ph | Ph | 5j | 11 min | 92 |

[a]Rearrangement reaction carried out at 75° C.;
[b]Isolated yield; and
[c]35% 2f remaining.

Since the rearrangement process requires ring expansion of one of the phenyl rings in the trityl group, it was considered that placement of an electron donating or withdrawing group in one of the three phenyl rings might influence the outcome of the reaction.

While the rearrangement should, in principle, be possible for any substituted N-benzyl propargyl alcohol 2, it was suspected that the steric environment of the N-atom might be crucial to the efficiency of both the activation and rearrangement processes. To address this question activation/rearrangement was carried out using substrates related to 2a in which the phenyls in the N-trityl group of 2a were sequentially replaced by H atoms (Table 2). The N-diphenylmethyl protected substrate 2m was readily converted into the corresponding acetate without significant formation of the corresponding N-acylated product. Interestingly, the acetate began to rearrange even at room temperature and, therefore, was not isolated. The rearrangement proceeded cleanly and completely in about 1 hour at 75° C. to give the expected tetracyclic product as a 5:1 mixture of diastereomers 5m-a/5m-b (44%) along with 27% of tricyclic compound 6m, which clearly arises via cyclopropane ring opening. This type of tricyclic compound has been reported. See J. J. Eisch, F. J. Gadek, J. Org. Chem., 1971, 36(22), 3376–3381. For the benzyl protected substrate 2n, problems were encountered in the O-acetate formation, due to competing N-acylation (or possibly O-acylation followed by acyl migration). This problem was alleviated by reaction of the lithium alkoxide of alcohol 2n with pivaloyl chloride to give the desired O-pivalate which was rearranged, in situ, at 75° C. (2 h) to give only the tricyclic compound 6n and none of the corresponding tetracycle (Table 2).

To further examine the N-protecting group effect, activation/rearrangement was carried out using dimethylphenylmethyl analogue 2o (replacement of two of the phenyls in the N-trityl group of 2a with methyl groups). Conversion of 2o into the corresponding acetate proceeded without incident, and the acetate was rearranged (75° C., ACN, 1 h) to give the expected tetracyclic compound 5o, but only as the minor product (Table 2). The major product of this reaction was characterized as a 1:1 diastereomeric mixture of 7o-a/7o-b. Interestingly, thermal rearrangement of the tert-butyl substrate 2p provided exclusively compound 7p (Table 2). Compounds 7o and 7p are formally products resulting from C—H insertion into a methyl group in the N-protecting groups of substrates 2o and 2p. The formation of compounds 7o and 7p in these reactions have vastly influenced our thinking regarding the probable mechanism of formation of tetracyclic products 5 in the general rearrangement process.

TABLE 2

Structural variation in the amino protecting group.

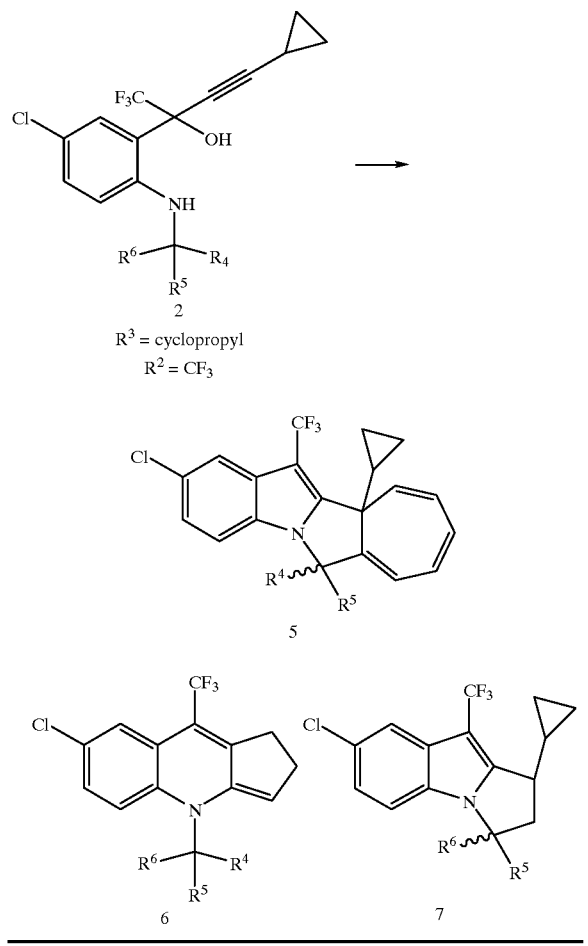

$R^3$ = cyclopropyl
$R^2$ = $CF_3$

| Substrate (2) | | | Product 5 | Product 6 | Product 7 |
|---|---|---|---|---|---|
| $R^4$ | $R^5$ | $R^6$ | (yield)[a] | (yield)[a] | (yield)[a] |
| 2a | Ph | Ph | Ph | 5a (84%) | — | — |
| 2m | H | Ph | Ph | 5m-a/5m-b (44%) | 6m (27%) | — |
| 2n[c] | H | H | Ph | — | 6n (51%)[b] | — |
| 2o | Me | Me | Ph | 5o (14%) | — | 7o-a/7o-b (71%) |
| 2p | Me | Me | Me | — | — | 7p (93%) |

[a]Isolated yield;
[b]33% 2n remaining; and
[c]Pivalate was utilized instead of acetate.

It is clear that the nature of the N-protecting group has a large effect on the efficiency of O-activation, and a profound influence on the rearrangement pathway. A general mechanistic scheme is proposed (Scheme 4) to account for the formation of tetracyclic products 5 from N-trityl protected propargyl alcohols 2 upon O-activation, and for the alternative modes of rearrangement observed with different N-protecting groups. For substrates with bulky N-protecting groups (2a, trityl; 2o, dimethylphenylmethyl; 2p, tert-butyl) it is proposed that O-activation results in slow C—O bond fission [There is a small primary kinetic isotope effect on the rate of rearrangement. $k_H/k_D$=1.7 for the rearrangement of 2a to 5a at 75° C., suggesting that the N—H bond fission is also occurring in the transition state for the reaction, at least to some extent.] and rearrangement to give a carbene intermediate 8 [H. -J. Rathjen, P. Margaretha, S. Wolff, W. C. Agosta, *J. Am. Chem. Soc.*, 1991, 113, 3904–3909.]. The carbene 8 undergoes cyclopropanation [W. von E. Doering, L. H. Knox, *J. Am. Chem. Soc.*, 1950, 72, 2305–2306.] followed by ring expansion to give the tetracyclic product 5 (trityl), or C—H insertion [(a) D. F. Taber, R. E. Ruckle, Jr., *J. Am. Chem. Soc.*, 1986,108, 7686–7693. and (b) G. A. Russell, D. G. Hendry,*J. Org. Chem.*, 1963,28, 1933–1935.] to give the product 7 (tert-butyl). Both modes of reaction operate when the protecting group contains both methyl and phenyl groups (dimethylphenylmethyl). In the cases of non hindered protecting groups, i.e. benzyl protection (2n, $R^4$=$R^5$=H, $R^6$=Ph), it is proposed that O-activation results in cyclization to give the highly strained intermediate 9, [(a) R. P. Johnson, *Chem. Rev.*, 1989, 89, 1111–1124. ; (b) R. C. Burrell, K. J. Daoust, A. Z. Bradley, K. J. DiRico, R. P. Johnson,*J. Am. Chem. Soc.*, 1996, 118, 4218–4219.; and (c) H. Hopf, H. Berger, G. Zimmermann, U. Nuchter, P. G. Jones, I. Dix, *Angew. Chem. Int. Ed. Engl.*, 1997,36(11), 1187–1190.] which undergoes ring opening of the cyclopropane, to give tricycle 6. Presumably, this mode of reaction is not observed for sterically demanding N-protecting groups due to significant steric interactions between the N-protecting group and the terminal acetylene substituent in the transition state for ring closure. In the case of a moderately hindered protecting group, i.e. diphenylmethyl protection (2m, $R^4$=H, $R^5$=$R^6$=Ph), it appears that both mechanisms are operating, to give both tetracyclic and tricyclic products. The precise mechanism for formation of the carbene 8 from the activated propargyl alcohol 2 is not clear. This could proceed in a concerted manner, via the stabilized carbocation 10, or via the o-quinodimethide 11 [(a) J. M. Wiebe, A. S. Caille, L. Trimble, C. K. Lau, *Tetrahedron*, 1996, 52(36), 11705–11724.; (b) Y. N. Gupta, M. J. Doa, K. N. Houk, *J. Am. Chem. Soc.*, 1982, 104, 7336–7338.; and (c) W. Verboom, B. G. van Dijk, D. N. Reinhoudt, *Tet. Lett.*, 1983,24(36), 3923–3926. d) D. J. Vanderzande, R. A. Ceustermans, H. J. Martens, S. M. Toppet, G. J. Hoornaert, *J. Org. Chem.*, 1983, 48, 2188–2193.]. Involvement of a stabilized carbocation 10 in a rate limiting step is unlikely on the basis of no solvent effect on the reaction rate and the observed terminal acetylene substituent effects (reaction proceeds at the same rate for all p-substituted phenyl groups on terminal acetylene, Table 1, entries 6–8); the carboethoxyl substrate 2c (Table 1, entry 2) rearranges quickly, yet substrates with alkyl substituents rearrange slowly (Table 1, entries 3–5). While attempts to trap an o-quinodimethide intermediate were not successful, the formation of 11 in the rate limiting step cannot be ruled out. [The observed $k_H/k_D$ could be consistent with slow formation of o-quinodimethide, however, when the rearrangement reactions was carried out in dimethylacetylene dicarboxylate, the rearrangement product was formed with no evidence of a Diels Alder adduct from reaction with the quinodimethide.] The rate limiting formation of the carbene 8 followed by rapid collapse to products is consistent with the observed terminal acetylene and propargyl steric and electronic substituent effects (substituents capable of conjugation to the carbene provide fast rearrangement). Finally, the absence of electronic effects for substituents in the trityl group (Scheme 3) is consistent with rapid and non selective intramolecular reaction of the carbene 8.

In conclusion, activation of tertiary propargyl alcohols of general structure 2 results in novel and facile rearrangement reactions providing products of phenyl cyclopropanation-ring expansion (tetracycles 5), C—H insertion (tricycles 7), or six membered ring formation accompanied by cyclopropane ring opening (tricycles 6). The distributions of products are readily explained in terms of the nature of the N-protecting group, in particular the availability of phenyl and methyl groups and the steric environment of the aniline moiety. The observed products in these rearrangement reactions and the observed substituent effects are consistent with reaction proceeding via a carbene intermediate, at least in the cases of bulky protecting groups. These highly efficient rearrangement processes take place under extremely mild conditions and enable the rapid assembly of novel heterocyclic structures which are not readily accessed using other methods. With appropriate choice of substituents, and N-protecting group, it should be possible to access each mode of rearrangement at will, to selectively provide new and potentially important nitrogen containing heterocycles.

SCHEME 4

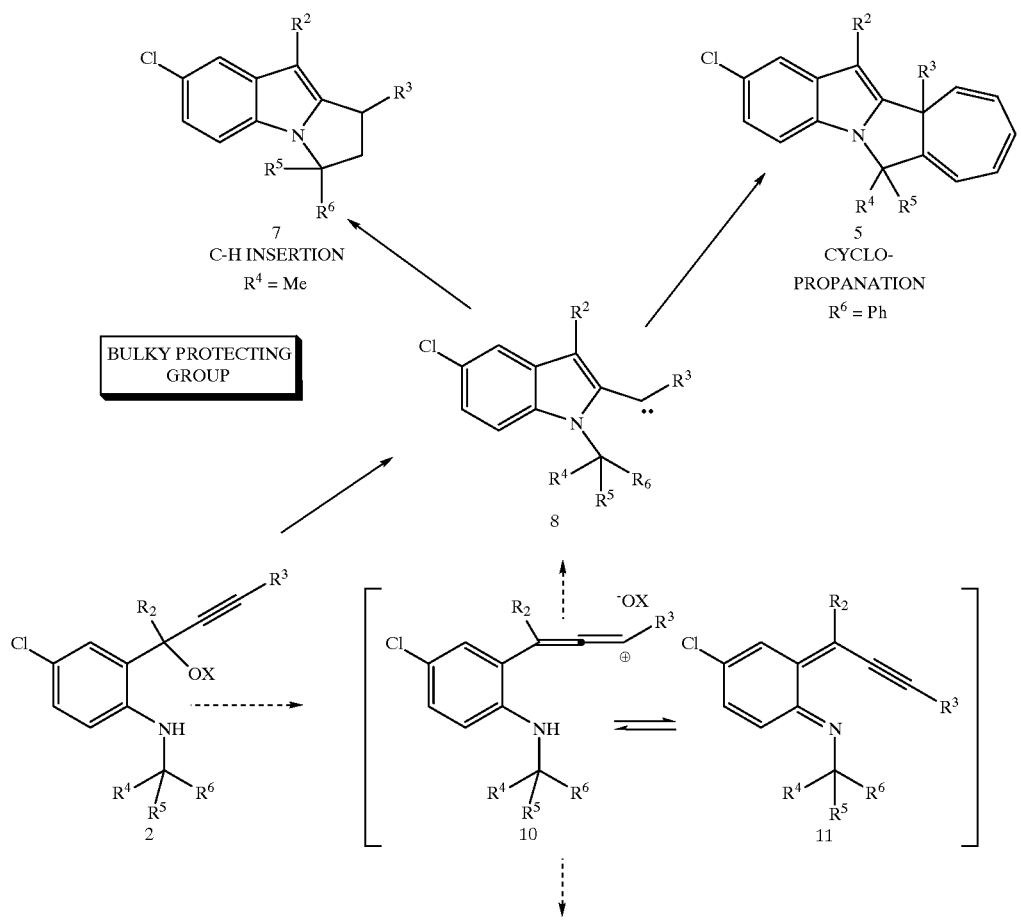

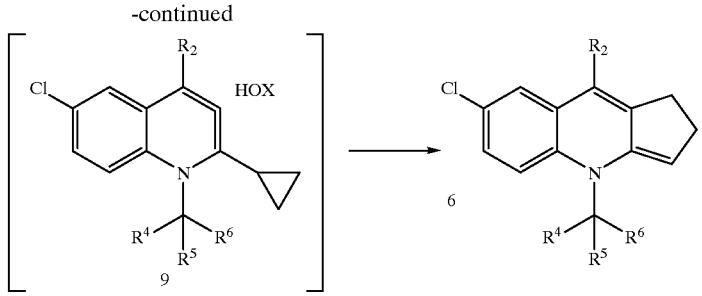

The compounds of Formula I and IV may be useful as markers in identifying impurities in a process for the preparation of efavirenz (1), which employed the cyclization of a compound of Formula III such that these compounds might be by-products produced. These compounds may also be useful as research tools to study the chemical and physical properties of these novel ring systems.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention.

EXAMPLE 1
Preparation of N-Trityl-4-Chloro-2-[Cyclopropylethynyl-Hydroxy-Trifluoromethyl]methylaniline 2a.

The N-protected amino alcohol, compound 2a, can be prepared following the procedures described in U.S. Pat. No. 5,633,405, 5,698,741, and 5,663,467, as well as M. E. Pierce, et al., *J. Org. Chem.*, 1998, 63, 8536–8543; and L. Tan, et al., *Angew. Chem. Int. Ed.*, 1999, 38, 711–713.

EXAMPLE 2
Preparation of Substituted Dihydrocyclohepta[3,4]Pyrrolo[12-a]Indole 5a.

To a solution of 2a (273 mg, 0.51 mmol) in $CH_3CN$ (10.3 mL) at 25° C. was added CDI (carbonyldiimidazole, 92 mg, 0.57 mmol) and the reaction was warmed to 30° C. After 20 min, the solution was quenched into saturated aqueous $NH_4Cl$ (15 mL), EtOAc (15 mL) was added, and the layers were separated. The aqueous phase was extracted with EtOAc (10 mL), and the organic phases were combined, washed with brine (15 mL), dried ($MgSO_4$), and concentrated. The crude product was purified by silica gel chromatography (eluted with EtOAc/hexanes) to give 244 mg 5a in 93% yield.

$^1$H NMR ($C_6D_6$) δ 8.06 (s, 1H), 7.19 (m, 2H), 7.08 (m, 2H), 7.01 (m, 3H), 6.88 (m, 3H), 6.83 (dd, J= 2.0, 8.8, 1H), 6.64 (d, J=8.8, 1H), 6.18 (m, 2H), 6.05 (m, 2H), 5.97 (d, J=10.1, 1H), 1.17 (m, 1H), 0.18 (m, 1H), 0.12 (m, 1H), 0.02 (m, 1H), −0.15 (m, 1H)

$^{13}$C NMR ($C_6D_6$) δ 147.9, 142.3, 140.9, 130.5, 130.2, 130.0, 129.0, 128.9, 128.7 (2C), 128.3, 128.1, 127.9, 126.1, 123.7, 123.3, 120.2, 113.6, 97.8 (m), 77.5, 52.1, 17.7, 5.3, 3.3.

HRMS calcd for $C_{32}H_{23}ClF_3N$ m/z 514.1549 found m/z 514.1549.

EXAMPLE 3
Preparation of Substituted Dihydrocyclohepta [3,4]Pyrrolo [1,2-a]Indole 5a.

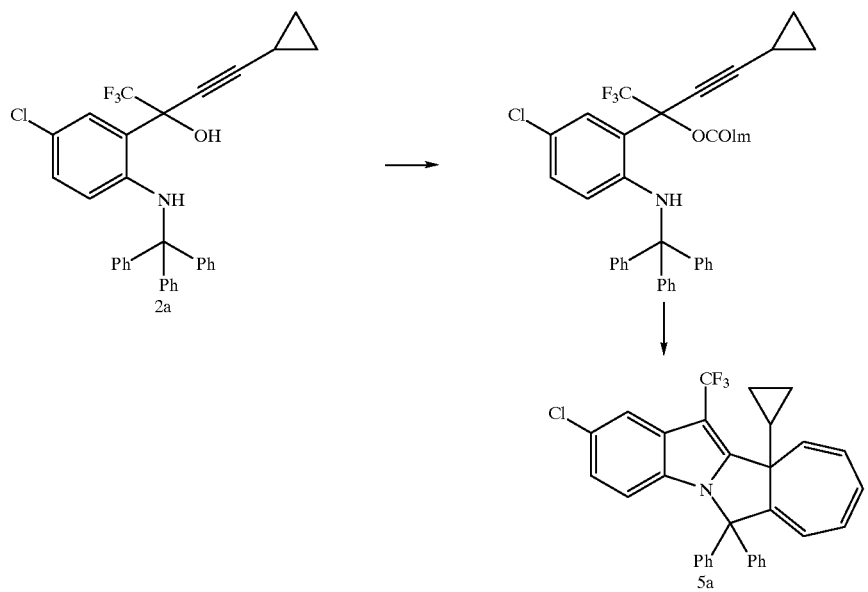

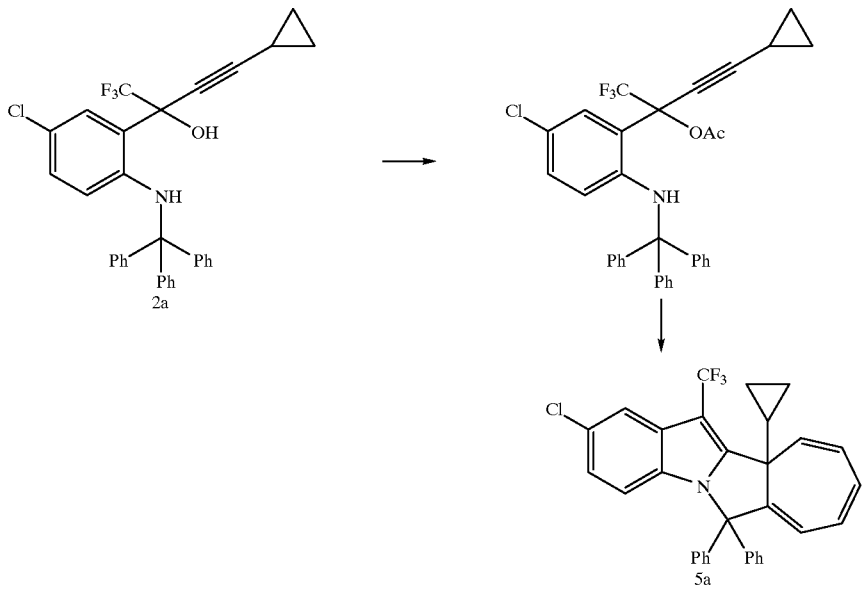

To a solution of 2a (273 mg, 0.51 mmol) in CH$_3$CN (10.3 mL) at RT was added acetic anhydride (58 μL, 0.62 mmol) followed by DIEA (134 μL, 0.77 mmol) and DMAP (catalytic amount). After 1 h, the solution was quenched into saturated aqueous NaHCO$_3$ (15 mL), EtOAc (15 mL) was added, and the layers were separated. The aqueous phase was extracted with EtOAc (10 mL), and the organic phases were combined, washed with water (15 mL) then brine (15 mL), dried (MgSO$_4$), and concentrated. A solution of the solid in ACN (10.3 mL) was warmed to 75° C. After 7.5 h, the solution was quenched into saturated aqueous NH$_4$Cl (15 mL), EtOAc (15 mL) was added, and the layers were separated. The aqueous phase was extracted with EtOAc (10 mL), and the organic phases were combined, washed with brine (15 mL), dried (MgSO4), and concentrated. The crude product was purified by silica gel chromatography (eluted with EtOAc/hexanes) to give 249 mg 5a in 95% yield.

$^1$H NMR (C$_6$D$_6$) d 8.06 (s, 1H), 7.19 (m, 2H), 7.08 (m, 2H), 7.01 (m, 3H), 6.88 (m, 3H), 6.83 (dd, J=2.0, 8.8, 1H), 6.64 (d, J=8.8, 1H), 6.18 (m, 2H), 6.05 (m, 2H), 5.97 (d, J=10.1, 1H), 1.17 (m, 1H), 0.18 (m, 1H), 0.12 (m, 1H), 0.02 (m, 1H), −0.15 (m, 1H).

$^{13}$C NMR (C$_6$D$_6$) d 147.9, 142.3, 140.9, 130.5, 130.2, 130.0, 129.0, 128.9, 128.7 (2C), 128.3, 128.1, 127.9, 126.1, 123.7, 123.3, 120.2, 113.6, 97.8 (m), 77.5, 52.1, 17.7, 5.3, 3.3.

HRMS calcd for C$_{32}$H$_{23}$ClF$_3$N m/z 514.1549 found m/z 514.1549.

What is claimed is:

1. A process for the preparation of a compound of Formula I:

wherein:

R$^1$ is: H, or halo;

R$^2$ is: C$_1$–C$_6$ alkyl, C$_1$–C$_6$ perfluoroalkyl, or phenyl;

R$^3$ is: H, C$_1$–C$_6$ alkyl, C$_3$–C$_6$ cycloalkyl, CO$_2$Et, phenyl, unsubstituted or substituted with one, two, or three substituents selected from C$_1$–C$_6$ alkyl, C$_1$–C$_6$ alkoxyl, and nitro;

R$^4$, R$^5$ and R$^6$ are H, C$_1$–C$_6$ alkyl, or phenyl, unsubstituted or substituted with one, two, or three R$^a$ substituents selected from: C$_1$–C$_6$ alkyl, C$_1$–C$_6$ alkoxyl, SO$_2$CH$_3$;

R$^{4a}$ is: H and R$^{4b}$ is H or C$_1$–C$_5$ alkyl, when R$^4$ is C$_1$–C$_6$ alkyl, or R$^{4a}$ and R$^{4b}$ substitutents together represent a ring of seven carbons with alternating double bonds, that is unsubstituted or substituted with one, two, or three R$^a$ substituents selected from: C$_1$–C$_6$ alkyl, C$_1$–C$_6$ alkoxyl, SO$_2$CH$_3$, when R$^4$ represents a phenyl, as defined above in R$^4$; and R$^7$ is: —CO(CH$_3$) or —CO(imidazolyl);

which comprises the steps of:

a) reacting a compound of Formula II

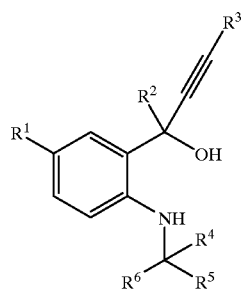

II with carbonyl diimidazole in an aprotic solvent, or with acetic anhydride in a solvent to produced a protected alcohol of Formula III:

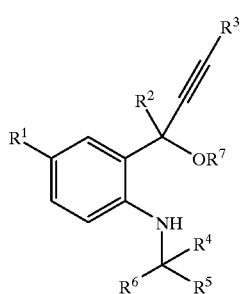

III b) heating the protected alcohol of Formula III in the presence or absence of a solvent, at a temperature of about 0° C. to about 100° C. to produce the compound of Formula I, with the proviso that when $R^3$ is cyclopropyl, $R^6$ is phenyl and only one of $R^4$ and $R^5$ is H.

2. A compound of Formula I:

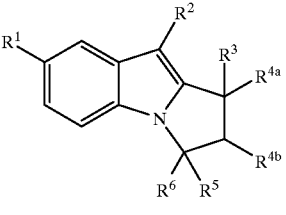

I wherein:
$R^1$ is: H, or halo;
$R^2$ is: $C_1$–$C_6$ alkyl, $C_1$–$C_6$ perfluoroalkyl, or phenyl;
$R^3$ is: H, $C_1$–$C_6$ alkyl, $C_3$–$C_6$ cycloalkyl, $CO_2Et$, phenyl, unsubstituted or substituted with one, two, or three substituents selected from $C_1$–$C_6$ alkyl, $C_1$–$C_6$ alkoxyl, and nitro;
$R^4$, $R^5$ and $R^6$ are H, $C_1$–$C_6$ alkyl, or phenyl, unsubstituted or substituted with one, two, or three $R^a$ substituents selected from: $C_1$–$C_6$ alkyl, $C_1$–$C_6$ alkoxyl, $SO_2CH_3$;
$R^{4a}$ is: H and $R^{4b}$ is H or $C_1$–$C_5$ alkyl, when $R^4$ is $C_1$–$C_6$ alkyl, or
$R^{4a}$ and $R^{4b}$ substitutents together represent a ring of seven carbons with alternating double bonds, that is unsubstituted or substituted with one, two, or three $R^a$ substituents selected from: $C_1$–$C_6$ alkyl, $C_1$–$C_6$ alkoxyl, $SO_2CH_3$, when $R^4$ represents a phenyl, as defined above in $R^4$, with the proviso that $R^1$ is not H, when $R^2$ and $R^4$ are methyl, $R^3$ is H or methyl, $R^{4b}$, $R^5$ and $R^6$ are H.

* * * * *